(12) United States Patent
Sunaoshi et al.

(10) Patent No.: US 9,572,537 B2
(45) Date of Patent: Feb. 21, 2017

(54) APPARATUS AND METHOD FOR CALCULATING PRESSURE DISTRIBUTION

(71) Applicant: Kabushiki Kaisha Toshiba, Minato-ku (JP)

(72) Inventors: Takamitsu Sunaoshi, Kanagawa-ken (JP); Hideki Nukada, Kanagawa-ken (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 405 days.

(21) Appl. No.: 14/155,623

(22) Filed: Jan. 15, 2014

(65) Prior Publication Data

US 2014/0200733 A1 Jul. 17, 2014

(30) Foreign Application Priority Data

Jan. 15, 2013 (JP) .................. 2013-004874

(51) Int. Cl.
*G05D 1/10* (2006.01)
*A61B 5/00* (2006.01)
(Continued)

(52) U.S. Cl.
CPC ........... *A61B 5/7275* (2013.01); *A61B 5/1036* (2013.01); *A61B 5/1115* (2013.01); *A61B 5/4023* (2013.01);
(Continued)

(58) Field of Classification Search
CPC ................. A61B 5/7275; A61B 5/51
(Continued)

(56) References Cited

U.S. PATENT DOCUMENTS

| 4,370,721 A | * | 1/1983 | Berenberg | ......... G05B 19/4083 318/572 |
| 4,985,947 A | * | 1/1991 | Ethridge | .............. A61G 7/1017 280/250.1 |

(Continued)

FOREIGN PATENT DOCUMENTS

| JP | 2009-142517 | | 7/2009 |
| JP | 2009-240775 | A | 10/2009 |
| JP | 2009-297462 | A | 12/2009 |

OTHER PUBLICATIONS

Knight et al, "Chair Alarm for Patient Fall Prevention based on Gesture Recognition and Interactivity", IEEE, pp. 3698-3701, 2008.*

(Continued)

*Primary Examiner* — Anil Khatri
(74) *Attorney, Agent, or Firm* — Oblon, McClelland, Maier & Neustadt, L.L.P.

(57) ABSTRACT

A support apparatus in which a distribution of a load for a user can be designated. The load occurs at body parts of the user by a stand-up motion. A processor calculates a projection position of a center of gravity of the user onto a floor, calculates a region of the floor where the projection position is to be included at the stand-up motion, calculates a target position in the region based on the distribution, and calculates a direction from the projection position to the target position. The target position is nearer to one body part of the user to which a larger load distribution is designated than on other body parts to which a smaller load distribution is designated. A designation direction for the user to bend the body in advance of the stand-up motion is output based on the direction.

17 Claims, 16 Drawing Sheets

(51) Int. Cl.
*A61B 5/103* (2006.01)
*A61B 5/11* (2006.01)
*G06T 7/00* (2006.01)

(52) U.S. Cl.
CPC ............ *A61B 5/743* (2013.01); *G06T 7/0046* (2013.01); *A61B 2560/0487* (2013.01); *A61B 2562/046* (2013.01); *G06T 2207/10028* (2013.01); *G06T 2207/10048* (2013.01); *G06T 2207/30196* (2013.01)

(58) Field of Classification Search
USPC .................................................. 700/300–304
See application file for complete search history.

(56) References Cited

U.S. PATENT DOCUMENTS

| | | | | |
|---|---|---|---|---|
| 5,930,152 | A * | 7/1999 | Dumont | B60N 2/0224 128/845 |
| 6,493,608 | B1 * | 12/2002 | Niemeyer | B25J 9/1689 606/130 |
| 6,711,455 | B1 * | 3/2004 | Holloway | A41H 3/007 700/131 |
| 6,862,762 | B1 * | 3/2005 | Johnson | A61B 6/0442 378/177 |
| 6,871,120 | B1 * | 3/2005 | Nivet | B60N 2/0224 297/154 |
| 7,233,872 | B2 * | 6/2007 | Shibasaki | A61B 5/11 33/512 |
| 7,321,811 | B1 * | 1/2008 | Rawls-Meehan | A47C 20/041 5/600 |
| 7,630,796 | B2 * | 12/2009 | Okada | B60G 17/0161 701/1 |
| 7,671,249 | B2 * | 3/2010 | Nishizawa | B25J 9/1065 370/350 |
| 7,702,481 | B2 * | 4/2010 | Dionne | A61G 7/015 700/302 |
| 7,706,920 | B2 * | 4/2010 | Wieland | G05B 19/19 318/568.17 |
| 8,423,201 | B2 * | 4/2013 | Burdette | H01Q 3/04 343/766 |
| 8,909,378 | B2 * | 12/2014 | Rawls-Meehan | A47C 20/041 5/616 |
| 9,398,990 | B2 * | 7/2016 | Richter | A61G 5/04 |
| 9,445,751 | B2 * | 9/2016 | Young | A61B 5/1115 |

OTHER PUBLICATIONS

Freiha et al, "Smart Assistive Accident Free Wheelchair System (SAAFWS)", IEEE, pp. 67-72, 2013.*
Goncalves et al, "Fully-Automated Strength, Agility and Endurance Tests Assessment: An Integrated Low Cost Approach Based on an Instrumented Chair", IEEE, pp. 1-6, 2014.*
Liao et al, "On the Mechanical Design and Control of a Self-Adaptive Exoskeleton Chair", IEEE, pp. 937-942, 2015.*
Reasons for Refusal issued Aug. 19, 2016, in Japanese Patent Application No. 2013-004874 (with English-language translation).

* cited by examiner

PROJECTION REGION

APPARATUS AND METHOD FOR CALCULATING PRESSURE DISTRIBUTION

CROSS-REFERENCE TO RELATED APPLICATION

This application is based upon and claims the benefit of priority from Japanese Patent Application No. 2013-004874, filed on Jan. 15, 2013; the entire contents of which are incorporated herein by reference.

FIELD

Embodiments described herein relate generally to a support apparatus and a support method.

BACKGROUND

For example, when an aged person stands up from a chair where he/she was seated, an apparatus for supporting his/her stand-up motion is proposed. In this apparatus, the stand-up motion is stably supported while the aged person's physical burden is reduced. However, if a person is not using his/her muscle strength for a long time, it is well known that the muscle strength of this part is quickly fallen. Namely, for a person having some remaining physical ability to stand up, over-support by this apparatus will make the person's muscle strength be fallen.

DETAILED DESCRIPTION

According to one embodiment, a support apparatus includes an input unit, a first calculation unit, a second calculation unit, a third calculation unit, a fourth calculation unit, and an output unit. The input unit designates a distribution of a load between right and left of a user. The load is occurred at body parts of the user by a stand-up motion of the user. The first calculation unit is configured to calculate a projection position of a center of gravity of the user onto a floor. The second calculation unit is configured to calculate a region of the floor where the projection position is to be included at the stand-up motion. The third calculation unit is configured to calculate a target position in the region based on the distribution. The target position is nearer to a first body part of the user to which larger distribution is designated than a second body part of the user to which smaller distribution is designated. The fourth calculation unit is configured to calculate a direction from the projection position to the target position. The output unit outputs a designation direction for the user to bend an upper body of the user in advance of the stand-up motion, based on the direction.

Various embodiments will be described hereinafter with reference to the accompanying drawings.

In the first embodiment, for example, while an aged person's physical burden is reduced, support for the aged person to stably stand up from a seat is performed. If a user (subject) has at least one normal body part with a remaining physical ability, the stand-up motion is supported so as to add a proper burden to the normal body part by urging the user to utilize the remaining physical ability.

Hereinafter, a scene to support the user's stand-up motion at a toilet will be explained as one example.

The First Embodiment

Figure 1:
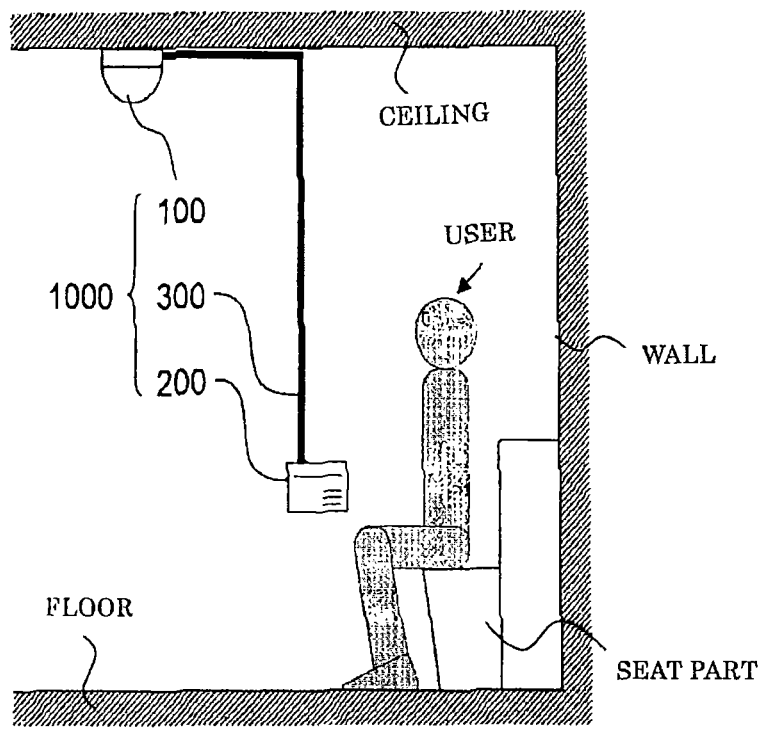
FIG. 1 is an overview diagram of a support apparatus according to the first embodiment.

FIG. 1 shows, in a toilet space surrounded by a wall, a floor and a ceiling, a situation that a user to be guided for stand-up motion sits down on a seat part (pedestal part) having a toilet bowl and a toilet seat. Moreover, in the first embodiment, as a timing to support the stand-up motion, from a condition that the user sits down on the seat part to a condition that the user begins to stand up, namely, a time until the user's buttocks are lifted off from the seat part is targeted.

FIG. 1 is an overview diagram of a support apparatus 1000 according to the first embodiment. The support apparatus 1000 includes a measurement unit 100 and a main unit 200 serially connected thereto via a serial communication cable 300. The measurement unit 100 is set up on the ceiling, and measures the user's position and posture. The main unit 200 having box-shape is set up on the wall to be reasonably within the user's touch from a condition that the user sits down on the seat part. While the user stands up the seat part, based on the user's physical feature, until the buttocks are lifted off as introduction of the stand-up motion, the support apparatus 1000 outputs a speech to guide the user's center of gravity to a suitable position. As a result, the user's stand-up motion is supported by balancing both the stability after buttocks are lifted off and the physical burden. Here, the burden is a force felt by the user as pain with stand-up motion, such as a reaction force against the floor, or a torque and a load occurred at the user's joint by self-weight thereof.

Figure 2:
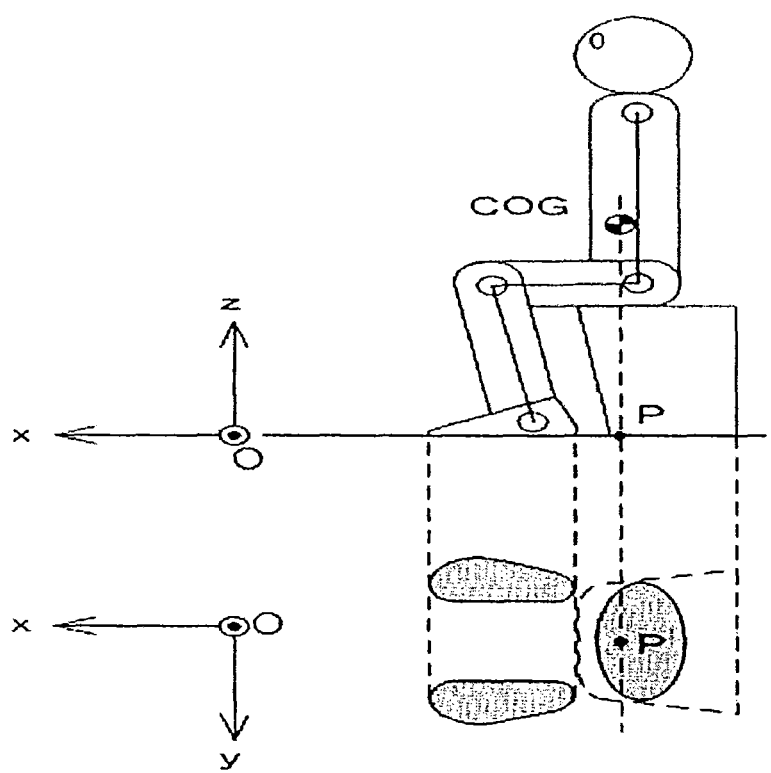
FIG. 2 is a schematic diagram to explain a coordinate system according to the first embodiment.

Here, definition of reference coordinate system will be explained. As shown in FIG. 2, a floor face is xy plane defined by x-axis and y-axis, a forward direction for the user to stand up is a positive direction along x-axis, and the user's left side while facing to the forward direction is a positive direction long y-axis. Furthermore, upper vertical direction is a positive direction along z-axis. Moreover, the origin O of the reference coordinate system is previously set at a predetermined position.

Figure 3:
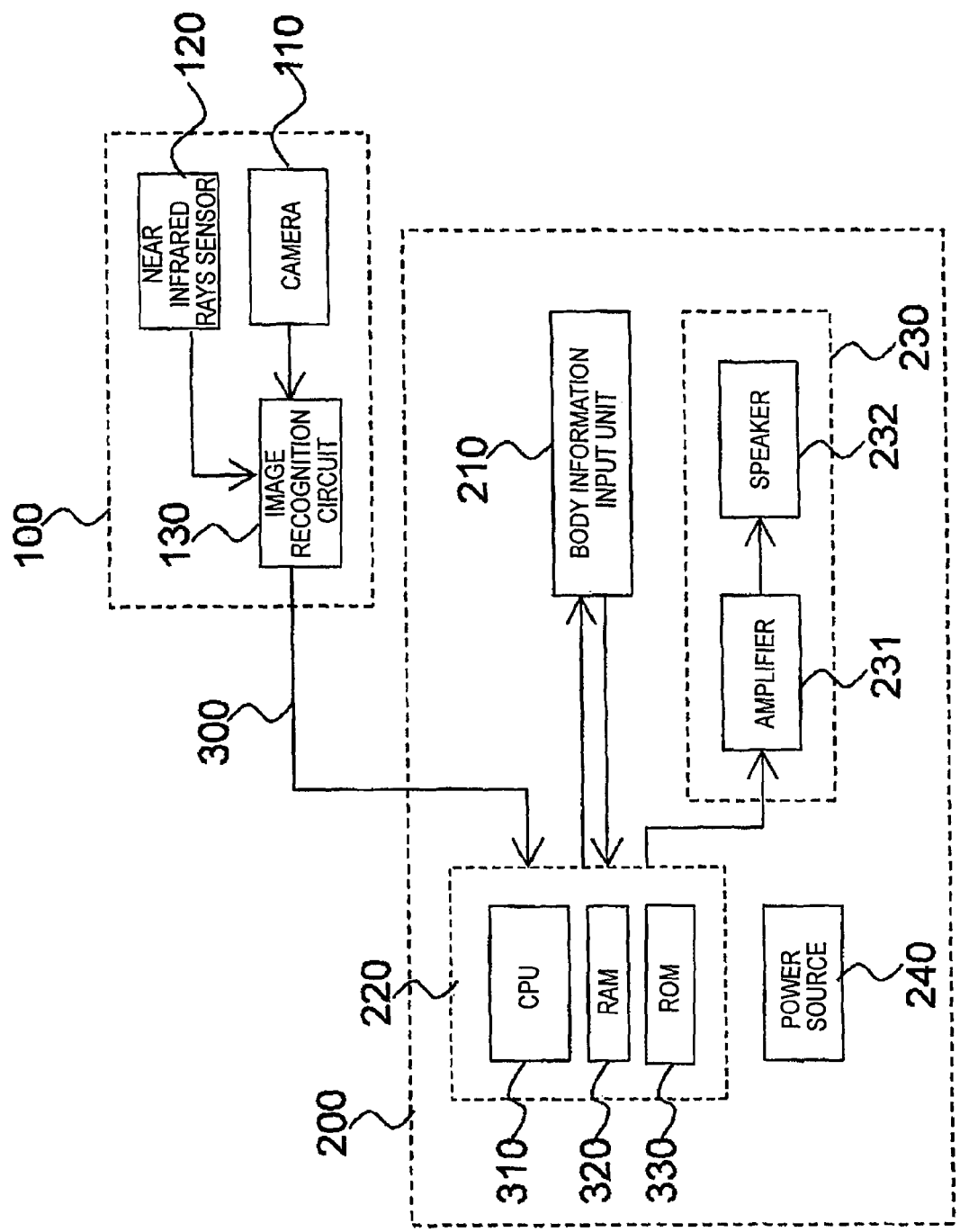
FIG. 3 is a block diagram of the support apparatus according to the first embodiment.

FIG. 3 is a block diagram of the support apparatus 1000. The measurement unit 100 measures a position and a posture of each body part of the user as the user's position and posture. Here, each body part includes a joint part, a part between joints, and a part extended from the joint, in human body. For example, the measurement unit 100 measures a position of each joint (position of body part), and a line segment connecting two joints or extended from the joint (posture of body part), as coordinates in the reference coordinate system.

As shown in FIG. 3, the measurement unit 100 includes a compound eye camera 110 to obtain the user's image, a near infrared-rays sensor 120 to measure a distance between each body part of the user and the camera 110, and an image recognition circuit 130 to digitize image information from the camera 110.

By using the image information from the camera 110, the image recognition circuit 130 extracts a moving part from differential region among images, and recognizes the moving part as a person (user). Furthermore, based on connection relationship of each body part of person previously stored in ROM 330 of the main unit 200, by matching each body part with the user's image, the user's each body part is decided.

Here, a depth of each body part is decided based on the image information from the camera 110. Furthermore, based on distance information from the near infrared-rays sensor 120, by correcting the distance between each body part and the camera 110, three-dimensional position and posture of each body part are obtained.

Specifically, a neck exists at a part connecting a head and a trunk, a shoulder exists at both side of the neck, and, based on information that a part extended from the shoulder (joint) is an arm, the arm can be recognized. If a bending part exists in the middle of the arm, this part is recognized as a knee (joint). Three-dimensional positions of the shoulder and the knee are measured, a line segment connecting the shoulder and the knee is an upper arm, and three-dimensional direction of the line segment is measured as the upper arm's posture. Moreover, the distance information can be corrected by measuring a distance between the near infrared-rays sensor 120 and an object (such as the floor, the seat part, or markers signed on the main unit 200) of which positional relationship from the sensor 120 is constant.

The image recognition circuit 130 digitizes the position and posture of each body part, and serially sends this position and posture information to the main unit 200.

As shown in FIG. 3, the main unit 200 includes a body information input unit 210 (including a touch panel set up on an upper face or a side dace of the main unit 200), an operation unit 220 (including CPU 310, RAM 320, ROM 330), a guide output unit 230 (including an amplifier 231 and a speaker 232), and a power source 240 (to supply a power to the input unit 210, the operation unit 220, the guide output unit 230 and the measurement unit 100).

The body information input unit 210 designates information (body information) representing physical feature selectively inputted by the user via the touch panel. This body information is information to relatively designate a distribution (balance) of loads (occurred at each body part of the user with stand-up motion) between front and back of the user, and between right and left of the user. For example, by using the body information input unit 210, the user selects which body part between front and back and which body part between right and left are relatively painful with stand-up motion, or designates a ratio of the pain as a level (item or numerical value). Namely, when the user stands up from the seat, as to a body part felt by the user as a painful part relatively, distribution of the load is designated as a smaller value. On the other hand, as to a body part felt by the user as an easy (normal) part relatively, distribution of the load is designated as a larger value.

Figure 4A:
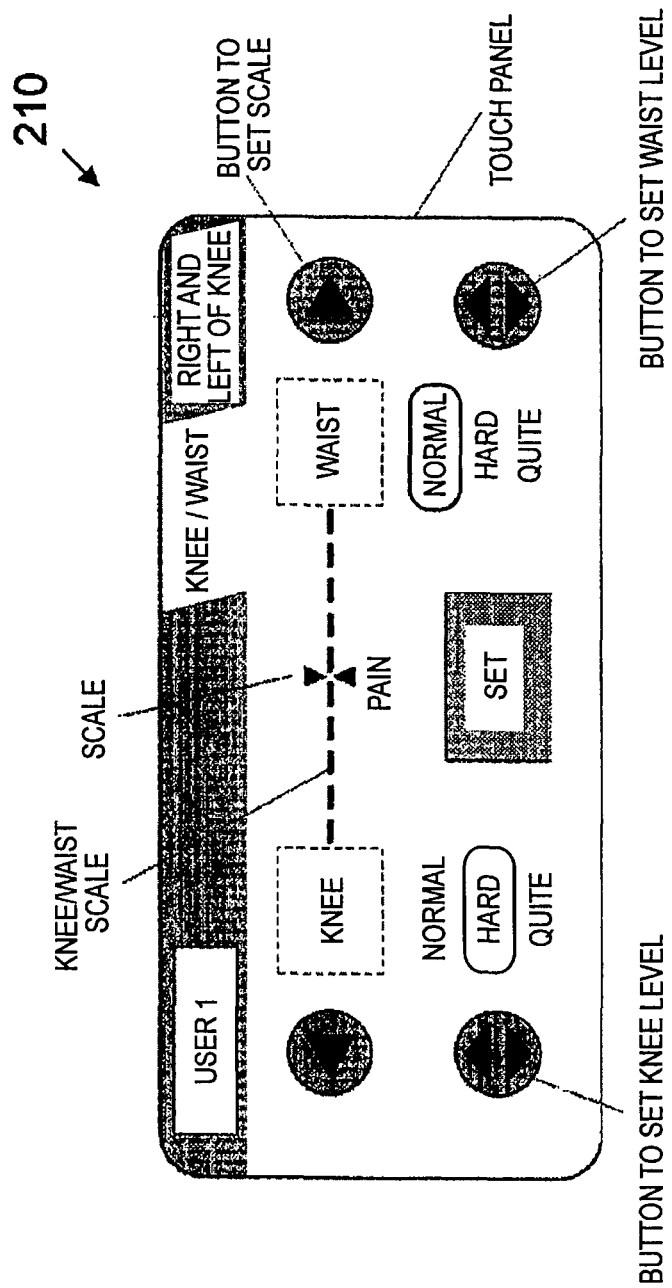
FIGS. 4A and 4B are examples of a screen set on a touch panel of a body information input unit according to the first embodiment.
Figure 4B:
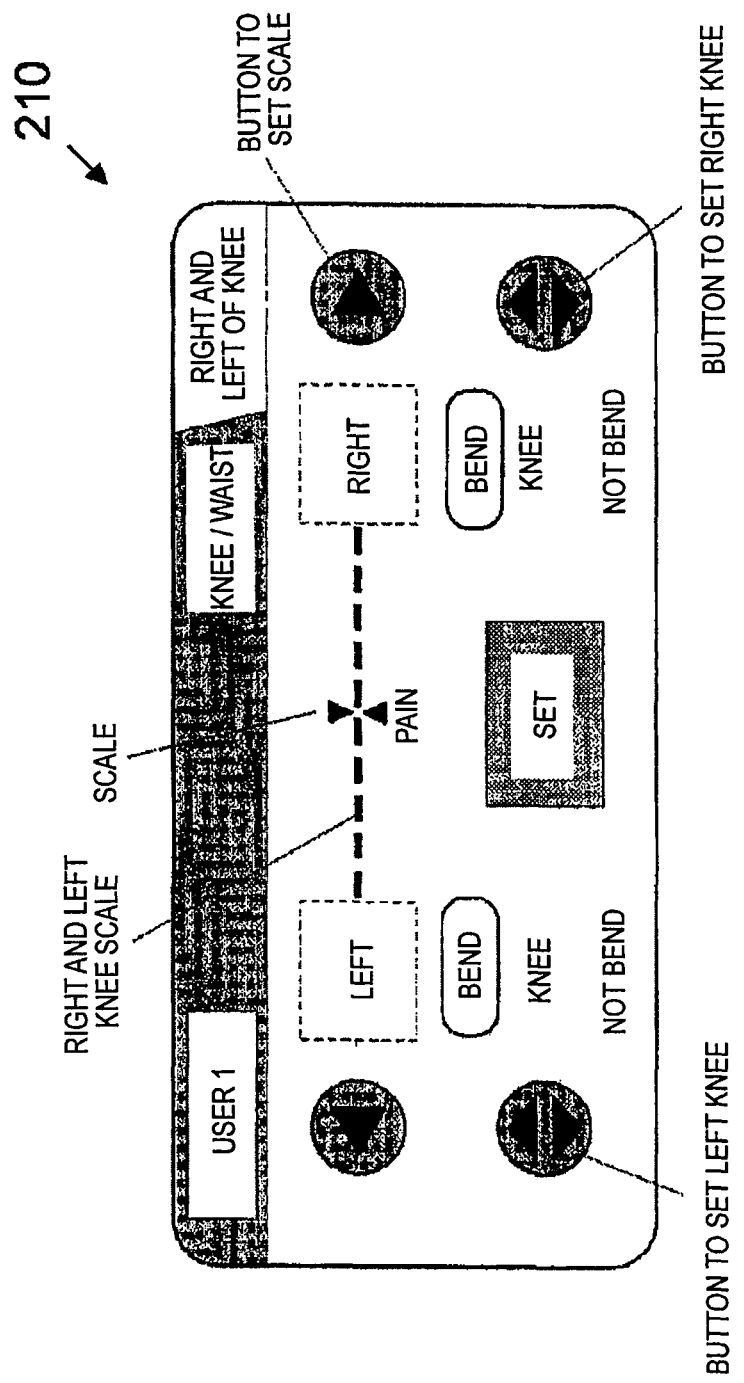

Concrete examples will be explained by using touch panel screens shown in FIGS. 4A and 4B. FIG. 4A shows the screen to set a distribution (balance between front and back) of loads occurred at knee and waist. FIG. 4B shows the screen to set a distribution (balance between right and left) of loads occurred at right knee and left knee. These screens can be switched by right upper menu.

In FIG. 4A, the user can select a pain (difficulty degree) to bend a hip joint (waist) and a pain to bend a knee joint as three levels (items) "normal", "hard" and "quite", respectively. This level is selected by pushing a button to set knee level and a button to set waist level respectively. If a level of difficulty degree of waist is equal to a level of difficulty degree of knee, the user can select which of difficulty degrees of knee and waist is larger by scale (numerical value). A gradation of scale can be moved by a button to set scale. If the gradation is positioned at a center of scale, both joints (knee and waist) have approximately equal difficulty degree. If the gradation is nearer to a body part name (knee or waist), the difficulty degree of this body part is larger.

In FIG. 4B, the user can select whether to bend a right knee and a left knee by a button to set right knee and a button to set left knee respectively. If a level set for right knee is equal to a level set for left knee, the user can set which of difficulty degrees (pain) to bend right knee and to bend left knee is larger by scale (numerical value). A gradation of scale can be moved by a button to set scale. If the gradation is positioned at a center of scale, both right knee and left knee have approximately equal difficulty degree. If the gradation is nearer to a body part name (right knee or left knee), the difficulty degree of this body part is larger.

In this way, information set by the user can be recorded in the RAM 320 of the operation unit 220 as body information. The body information can be recoded in correspondence with each user respectively. Furthermore, by inputting the user's height and weight, they can be recorded as the body information. Information of height and weight is used for correcting/confirming the position and posture of body part measured by the measurement unit 100.

Based on position and posture information (sent by the measurement unit 100) and body information (obtained by the body information input unit 210), the operation unit 220 calculates an amount of guide of the user's center of gravity and a direction thereof, i.e., a guide vector, and supplies guide information to the guide output unit 230 based on the result.

Figure 5:
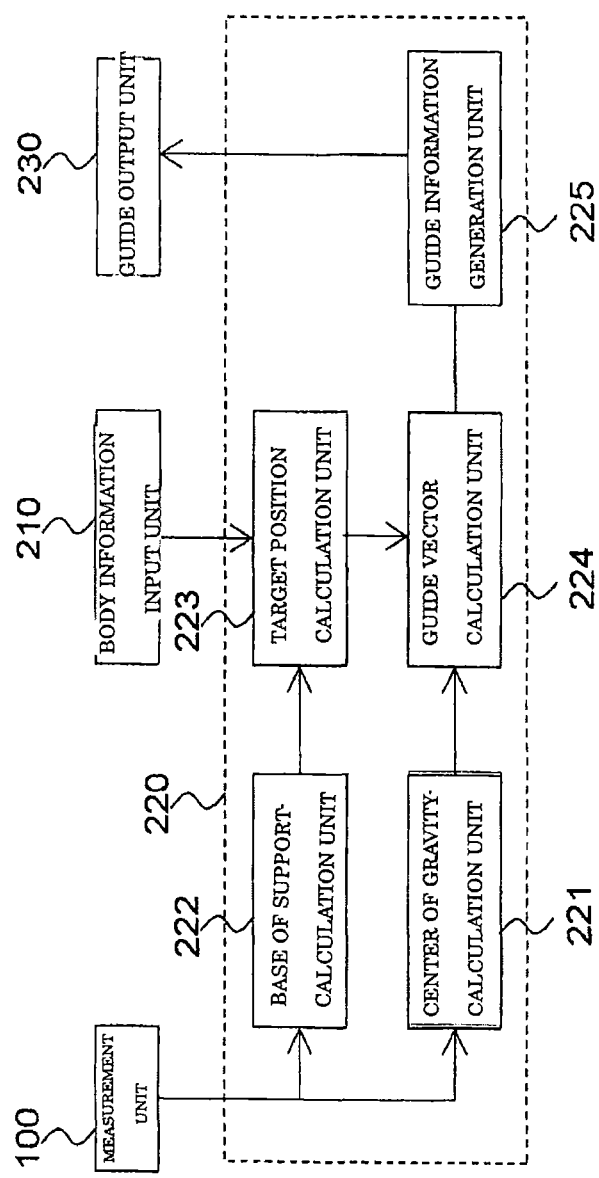
FIG. 5 is a block diagram of an operation unit according to the first embodiment.

FIG. 5 is a block diagram of the operation unit 220. As shown in FIG. 5, the operation unit 220 includes a center of gravity-calculation unit 221, a base of support-calculation unit 222, a target position calculation unit 223, a guide vector calculation unit 224, and a guide information generation unit 225.

The center of gravity-calculation unit (first calculation unit) 221 calculates the user's projection position of COG (center of gravity) based on the position and posture information (sent by the measurement unit 100). The base of support-calculation unit (second calculation unit) 222 calculates the user's base of support based on the position and posture information. The target position calculation unit (third calculation unit) 223 calculates a target position to guide the user's projection position of COG based on the base of support and the body information (sent by the body information input unit 210). The guide vector calculation unit (fourth calculation unit) 224 calculates a guide vector based on the user's projection position of COG and the target position. The guide information generation unit (generation unit) 225 generates guide information based on the guide vector.

For example, in the operation unit 220, the CPU 310 reads control program from the ROM 330, and extends this control program onto the RAM 320. This control program is functioned as the center of gravity-calculation unit 221, the base of support-calculation unit 222, the target position calculation unit 223, the guide vector calculation unit 224 and the guide information generation unit 225. Moreover, for example, each processing in following explanation is executed at a predetermined sampling interval in a period from start time of guide to completion thereof, after the user designates a guide start by operating a touch panel of the body information input unit 210.

The center of gravity-calculation unit 221 obtains the position and posture information from the measurement unit 100, and calculates a coordinate of the user's center of gravity in the reference coordinate system, based on the position and posture information. Here, for example, statistical weight ratio and center of gravity of each body part by sex and age are referred as reference information, a position vector to the user's center of gravity of each body part is calculated, and a total vector of all body parts (sum of moment vector of each body part) is calculated by multiplying the position vector with the weight ratio of each body part included in the reference information. This total vector is a position vector to the user's center of gravity. Based on the total vector, the center of gravity-calculation unit 221 calculates a coordinate of the user's center of gravity. Furthermore, the center of gravity-calculation unit 221 calculates a coordinate (xp,yp) of a projection position P of COG in the reference coordinate system by using the coordinate of the center of gravity. Here, the projection position P of COG is COG projected onto a floor face (z=0). The reference information is, for example, previously stored in the ROM 330.

Figure 6:
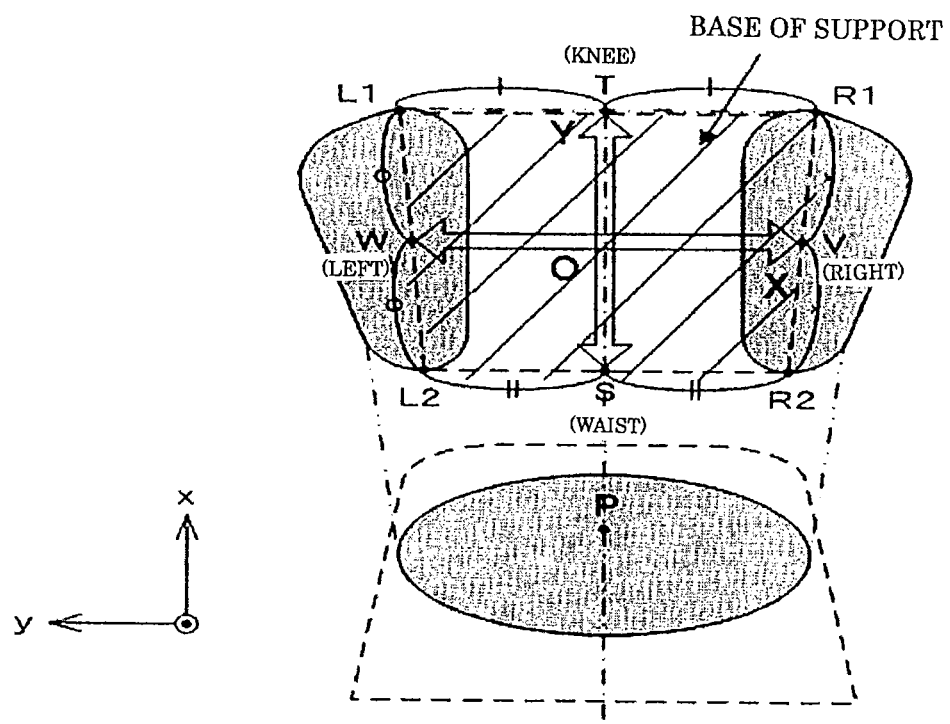
FIG. 6 is a schematic diagram to explain a base of support according to the first embodiment.

The base of support-calculation unit 222 obtains the position and posture information from the measurement unit 100, and calculates the user's base of support after the user's buttocks are lifted off from the seat part, based on the position and posture information. In general, the base of support is a region including a person's projection position of COG at a timing of the person's stand-up motion, i.e., a region surrounding parts where the person contacts. For example, when the user sits down on the seat part, as shown in two-dot chain line of FIG. 6, a region surrounding a part where both feet contact the floor face and a part where the user's buttocks contact the seat is the base of support. Here, when the user's buttocks are lifted off from the seat part, the base of support surrounding a region where both feet contact the floor face is calculated. Furthermore, as an example, a region surrounded by four feature points of toe positions and heel positions of both feet is approximately calculated as the base of support.

The base of support-calculation unit 222 calculates coordinates of toe positions and heel positions of the user's both feet on the floor face (z=0) in the reference coordinate system, i.e., a point L1 of toe position of left foot, a point L2 of heel position of left foot, a point R1 of toe position of right foot, and a point R2 of heel position of right foot. For example, by referring to the position and posture information, among line segments equivalent to the user's foot contacting the floor face, a maximum point along x-direction is a toe position, a minimum point along x-direction is a heel position, and each coordinate thereof is calculated. Moreover, if the measurement unit 100 cannot measure a posture of the user's foot and if the position and posture information is insufficient, each coordinate can be calculated by interpolating from positions of leg joints measured and foot size previously registered.

The base of support-calculation unit 220 calculates a line segment connecting a middle point T between two points L1 and R1 and a middle point S between two points L2 and R2 as an axis to adjust waist/knee load (X-axis) to set load-distribution between knee and waist (balance between front and back). Furthermore, the base of support-calculation unit 220 calculates a line segment connecting a middle point W between two points L1 and L1 and a middle point V between two points R1 and R2 as an axis to adjust knee load (Y-axis) to set load-distribution between right knee and left knee (balance between right and left). A coordinate of an intersection point between X-axis and Y-axis is set to the origin O, and a coordinate system (base of support-coordinate system) defined by X-axis and Y-axis is set. In the base of support-coordinate system, coordinates representing a region surrounded by four feature points is stored as the base of support into the RAM 320. Here, the Ram 320 stores information representing the base of support-coordinate system.

Based on the base of support (obtained by the base of support-calculation unit 222) and the body information (set by the body information input unit 210), the target position calculation unit 223 calculates a target position to guide the user's projection position of COG in the base of support immediately before (or immediately after) lifting-off the user's buttocks. Specifically, based on load-distribution designated by the body information, a target position to distribute load occurred at each body part related to the user's stand-up motion is calculated. Namely, the target position is calculated so as to make larger load be occurred at a body part to which larger load-distribution is designated than a body part to which smaller load-distribution is designated.

In the first embodiment, the target position is calculated so that, if a larger level to set load is designated to a body part by the body information, smaller load is distributed to the body part. On the other hand, the target position is calculated so that, if a smaller level to set load is designated to a body part by the body information, larger load is distributed to the body part.

For example, if a level to set load to waist is larger than a level to set load to knee by the body information input unit 210, x-coordinate of a target position in the base of support-coordinate system is set on a line segment connecting two points L2 and R2 at the back side in the base of support, so that load-distribution to knee is larger than load-distribution to waist. Conversely, if a level to set load to waist is smaller than a level to set load to knee, x-coordinate of a target position is set on a line segment connecting two points L1 and R1 at the forward side in the base of support, so that load-distribution to waist is larger than load-distribution to knee. If a level to set load to waist is equal to a level to set load to knee, based on a value set by gradation position of knee/waist scale, a coordinate proportionally distributed on a line segment TS connecting two points T and S is set to X-coordinate Xq of the target position. Namely, X-coordinate Xq of the target position is set at a position relatively near a body part to which a large level to set load (load-distribution is small) is designated and relatively far from a body part to which a small level to set load (load-distribution is large) is designated. As a result, as for a user who feels abnormality at knee, by keeping the projection position of COG at normal waist side (back side) in the base of support, a larger burden is imposed on waist than knee, and a burden imposed on knee at stand-up motion can be reduced. Conversely, as for a user who feels abnormality at waist, by keeping the projection position of COG at normal knee side (forward side) in the base of support, a larger burden is imposed on knee than waist, and a burden imposed on waist at stand-up motion can be reduced.

Furthermore, if the level is set as that right knee cannot be bent and left knee can be bent by the body information input unit 210, y-coordinate of a target position in the base of support-coordinate system is set on a line segment connecting two points L1 and L2 at the left side in the base of support, so that load-distribution to left knee is larger than load-distribution to right knee. Conversely, if the level is set as that left knee cannot be bent and right knee can be bent, y-coordinate of a target position is set on a line segment connecting two points R1 and R2 at the right side in the base of support, so that load-distribution to right knee is larger than load-distribution to left knee. If the level is set as that right knee and left knee can be bent, based on a value set by gradation position of right knee/left knee scale, a coordinate reverse-proportionally distributed on a line segment WV connecting two points W and V is set to Y-coordinate Yq of the target position. Namely, Y-coordinate Yq of the target position is set at a position relatively far from a body part to which a large level to set load (load-distribution is small) is designated and relatively near a body part to which a small level to set load (load-distribution is large) is designated. As a result, as for a user who feels abnormality at right knee, by keeping the projection position of COG at normal left knee side (left side) in the base of support, a larger burden is imposed on left knee than right knee, and a burden imposed on left knee at stand-up motion can be reduced. Conversely, as for a user who feels abnormality at left knee, by keeping the projection position of COG at normal right knee side (right side) in the base of support, a larger burden is imposed on right knee than left knee, and a burden imposed on left knee at stand-up motion can be reduced.

Figure 7:
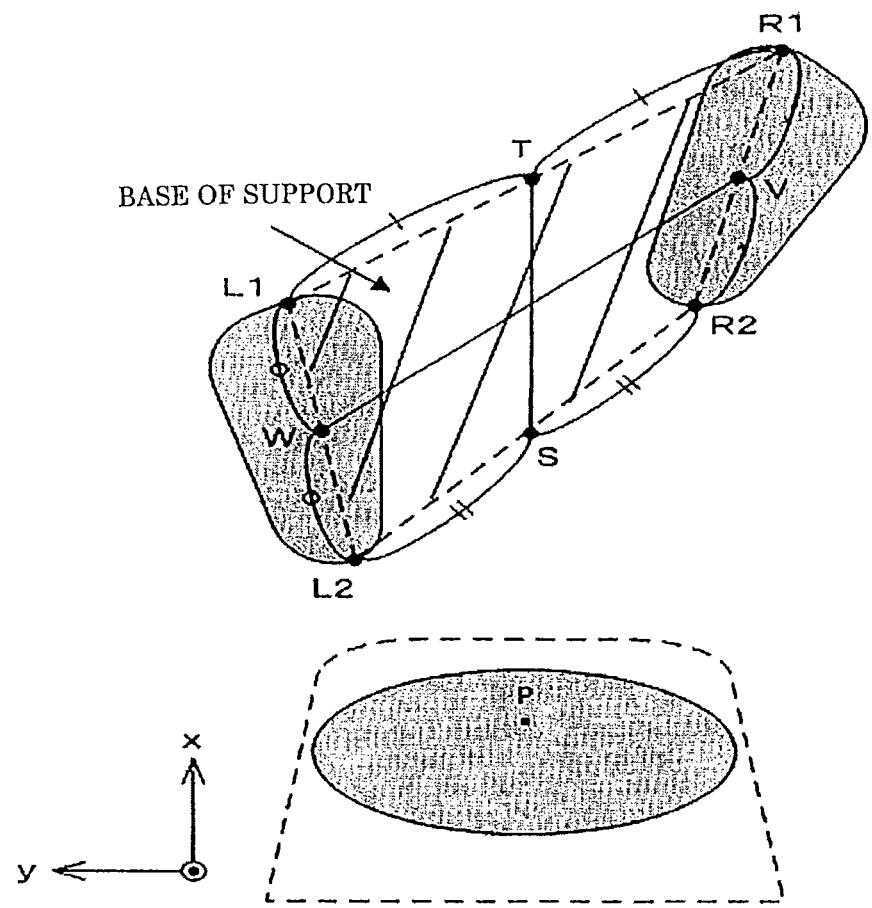
FIG. 7 is another schematic diagram to explain the base of support according to the first embodiment.

As mentioned-above, a coordinate (Xq,Yq) of the target position Q is determined in the base of support. Moreover, as shown in FIG. 7, an axis to the adjust waist load and an axis to adjust the knee load (virtually set on the base of support) are changed by a shape of the base of support. A method for setting a coordinate of the target position will be explained.

Based on the user's projection position of COG (calculated by the center of gravity-calculation unit 221) and the target position (calculated by the target position calculation unit 223), the guide vector calculation unit 224 calculates a guide vector (a direction to guide the user's projection position of COG and an amount thereof). Here, for example, a coordinate (xq, yq) of a target position Q' in the reference coordinate system is calculated by converting the coordinate (Xq,Yq) of the target position Q, and a vector (xq−xp, yq−yp) directing from a projection position P of COG to the target position Q' is calculated as the guide vector.

Based on the guide vector (calculated by the guide vector calculation unit 224), the guide information generation unit 225 generates guide information to be presented to the user in order to guide the user's COG to the target position. This guide information is supplied to the guide output unit 230. Namely, in the first embodiment, the guide information generation unit 225 selects a speech file most similar to the guide vector from a plurality of speech files previously stored in the ROM 330, and generates the guide information to be supplied to the guide output unit 230, based on the speech file. For example, if x-component (xq−xp) of the guide vector is positive value and if absolute value thereof is larger than absolute value of y-component (yq−yp), guide to forward is subjective. Accordingly, speech file to bend forward such as "Please bend your upper body forward" is selected. Conversely, if absolute value of y-component (yq−yp) is larger than absolute value of x-component (xq−xp), speech file to bend to any of right and left directions is selected based on whether y-component is positive value or negative value. If absolute value of y-component is equal to absolute value of x-component, speech file to bend to inclination direction such as "Please bend right-forward" is selected. In this way, guide information is selected based on direction and amount of the guide vector, and the guide information is suitably synthesized to be generated.

The guide output unit 230 obtains guide information (speech file) from the guide information generation unit 225, and outputs a speech based on the speech file via an amplifier 231 and a speaker 232. By presenting a guide direction to bend upper body before stand-up motion to the user via this speech, the user's COG is guided to the target position.

According to the support apparatus 1000 or the support method of the first embodiment, while stability at timing of stand-up motion is secured, balance of load occurred at each body part with the stand-up motion can be adjusted. As a result, in support of the stand-up motion, utilization of remaining physical ability can be urged to the user without over-support.

(The First Modification)

In the first embodiment, as the guide output unit 230, guide by speech was explained as an example. However, the support method is not limited to this example. For example, a support method for displaying information to the user by a screen, or a support method for guiding the user's COG by moving a seat part or a handrail, can be applied.

Figure 8:
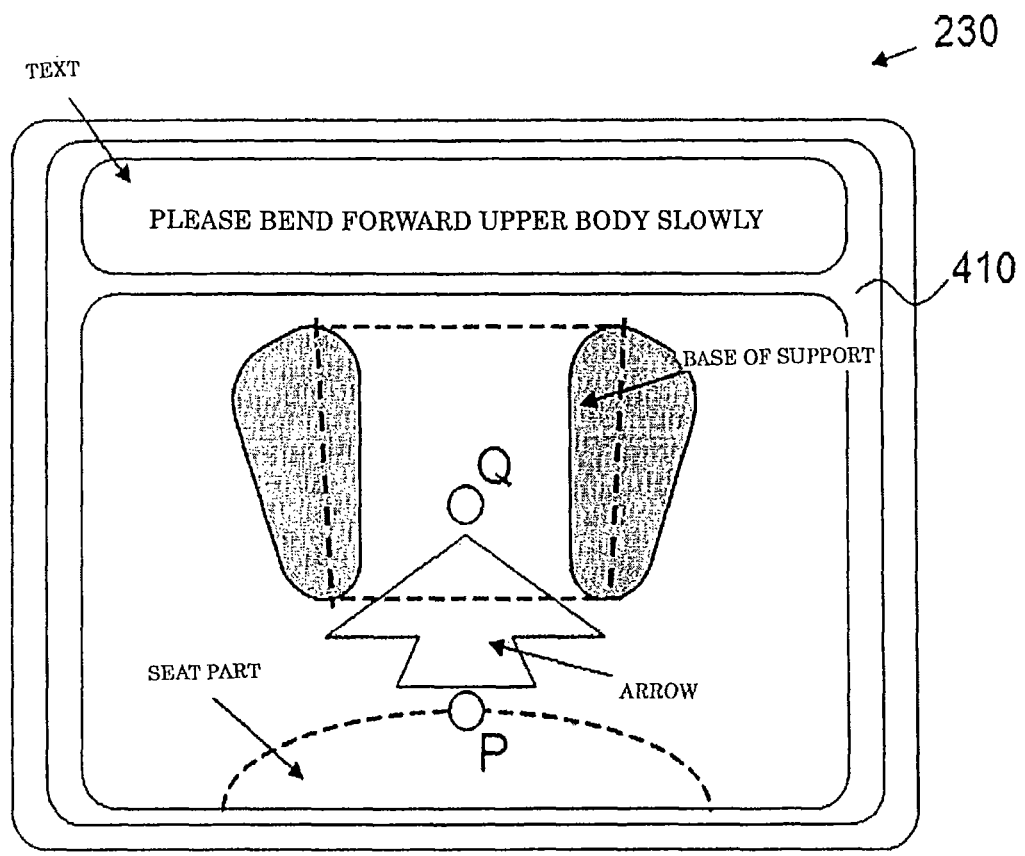
FIG. 8 is a schematic diagram to explain a guide output unit according to a first modification of the first embodiment.

FIG. 8 shows the case that a support method by the guide output unit 230 is displaying information via a display 410. The display 410 is equipped on a wall downwardly in front of the user sitting down. When the user's projection position of COG is moved forward by bending the user's upper body, if the user's line of sight is turned downwardly, the user's posture is natural. Accordingly, the display 410 is slightly set at the lower side. A position to set the display' may be suitably corrected by a distance between the seat part and the wall, or the user's height and visual acuity. On the display 410, a text representing guide content, the user's projection position P of COG, a target position Q to guide the projection position of COG, positions of the base of support and the seat part, and an arrow (guide direction and amount thereof) representing the guide vector, are displayed. Here, the user's projection position of COG is displayed hourly while the user is being guided. Accordingly, the user can easily decide which degree the user must bend the upper body until the target position. Even if a guide to pull foot is generated, the present position of foot and a destination position to pull foot are displayed. Accordingly, high guide effect easy for the user to recognize is expected.

(The Second Modification)

Figure 9:
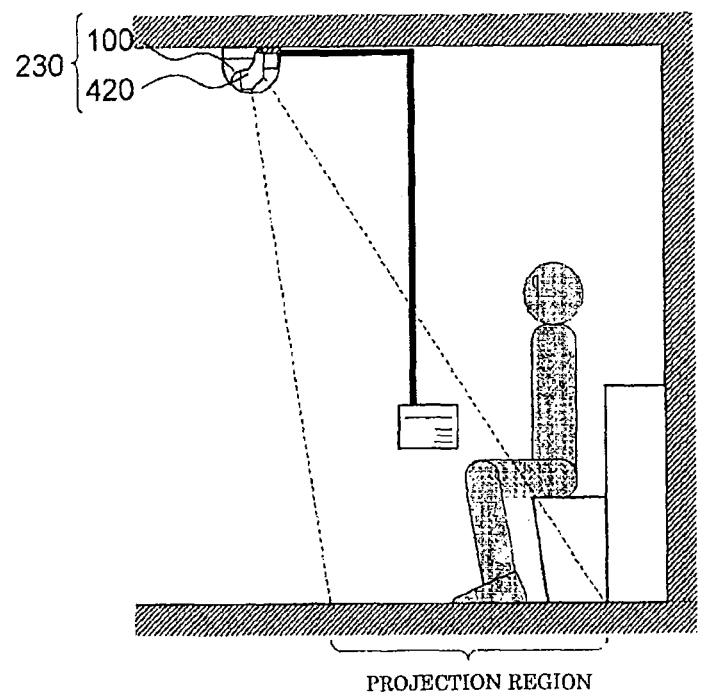
FIG. 9 is a schematic diagram to explain the guide output unit according to a second modification of the first embodiment.

FIG. 9 shows the case that a support method by the guide output unit 230 is display projected by a projector 420. The projector 420 is set on the ceiling, and equipped with the measurement unit 100 as one unit. The same display content as the display 410 (explained in the first modification) can be displayed forward from the user on the floor face. Furthermore, by previously detecting positional relationship among a projection region, the floor face and the seat part, the base of support and the projection position of COG (calculated by the operation unit 220) can be displayed with actual scale and position. For example, when a guide to correct the foot position is generated, a destination position to actually move the foot is displayed. Here, this display position is easy for the user to recognize and match the user's foot therewith. As a result, higher guide effect is expected. Furthermore, the measurement unit 100 and the projector 420 are equipped as one unit. Accordingly, miniaturization of the apparatus and space-saving of set position in toilet space can be realized.

(The Third Modification)

Figure 10:
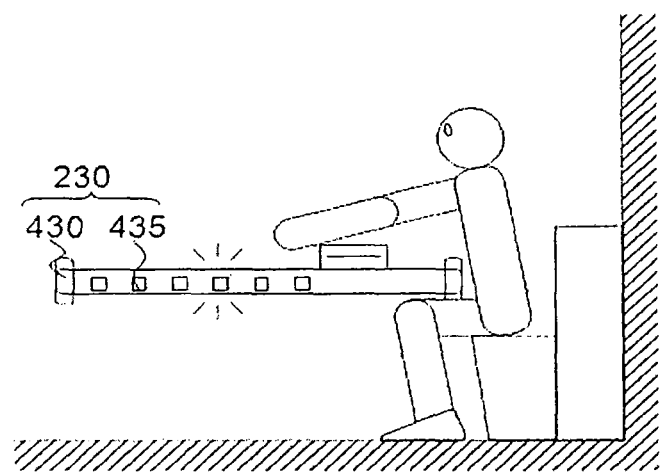
FIG. 10 is a schematic diagram to explain the guide output unit according to a third modification of the first embodiment.

FIG. 10 shows the case that a support method by the guide output unit 230 is a designation presented by a handrail 430 having a plurality of indicators (signal parts) 435. On the handrail 430 installed on the wall, an indicator (LED unit) 435 is equipped at a predetermined interval. This indicator 435 specifies a direction to bend the user's upper body and an amount to bend the user's waist forward. Namely, for example, by signaling (emitting) the indicator 435 at a position for the user to grasp the handrail 430, a direction to bend the upper body can be recognized by the user. Furthermore, for example, based on an amount of the guide vector, if the amount to bend the waist is large, the indicator set at farer position from the user is signaled. On the other hand, if the amount to bend the waist is small, the indicator set at nearer position to the user is signaled. As a result, the amount to bend the waist can be easily recognized by the user.

Furthermore, by guiding the user to grasp the handrail 430 by stretching the user's hand forward, the user can easily bend the upper body. By adjusting a position to emit the indicator 435, a position for the user to grasp is changed, and a degree to bend the upper body can be adjusted. As a result, the user's GOP can be effectively guided. By setting a color of the indicator 435 to yellow while the user is being guided, and by setting the color to green after the user is guided, the user can be more effectively guided. In not only the case that the handrail 430 is installed on one side of the wall but also the case that the handrail 430 is respectively installed on right and left sides of the wall, by emitting the indicator 435 at both sides, the user's both arms can be respectively guided to the handrail. As a result, a range of the base of support can be wider after lifting-off buttocks, and the user's stability can be improved.

The Second Embodiment

As the guide information generated by the guide information generation unit 225, a guide to urge the user to correct the base of support (position of both feet) calculated by the base of support-calculation unit 222, or a guide to urge the user to correct the guide vector (sit-down posture) calculated by the guide vector calculation unit 224, may be included.

Figure 11A:
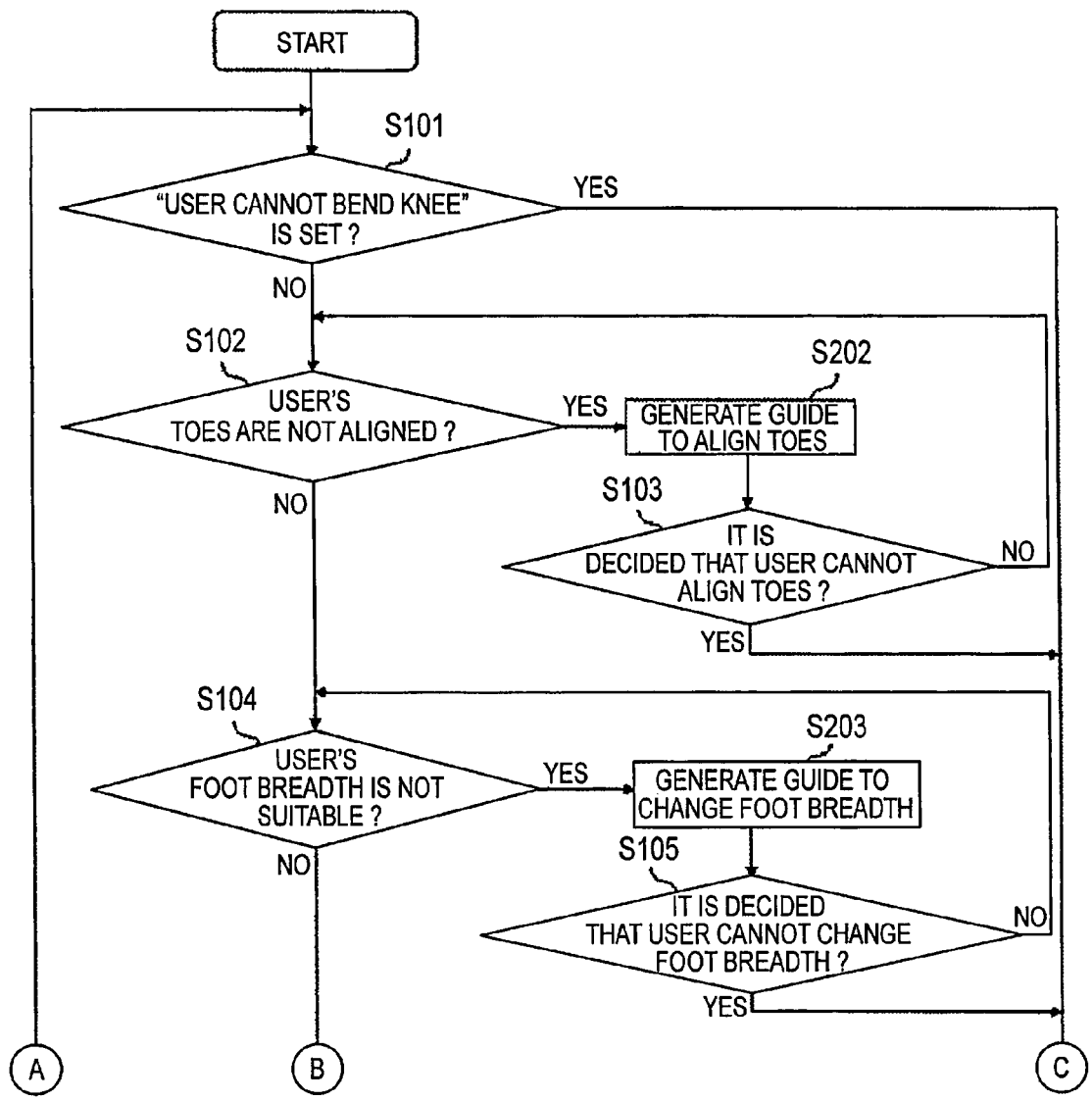
FIGS. 11A and 11B are flow chart of processing of a guide information generation unit according to the second embodiment.
Figure 11B:
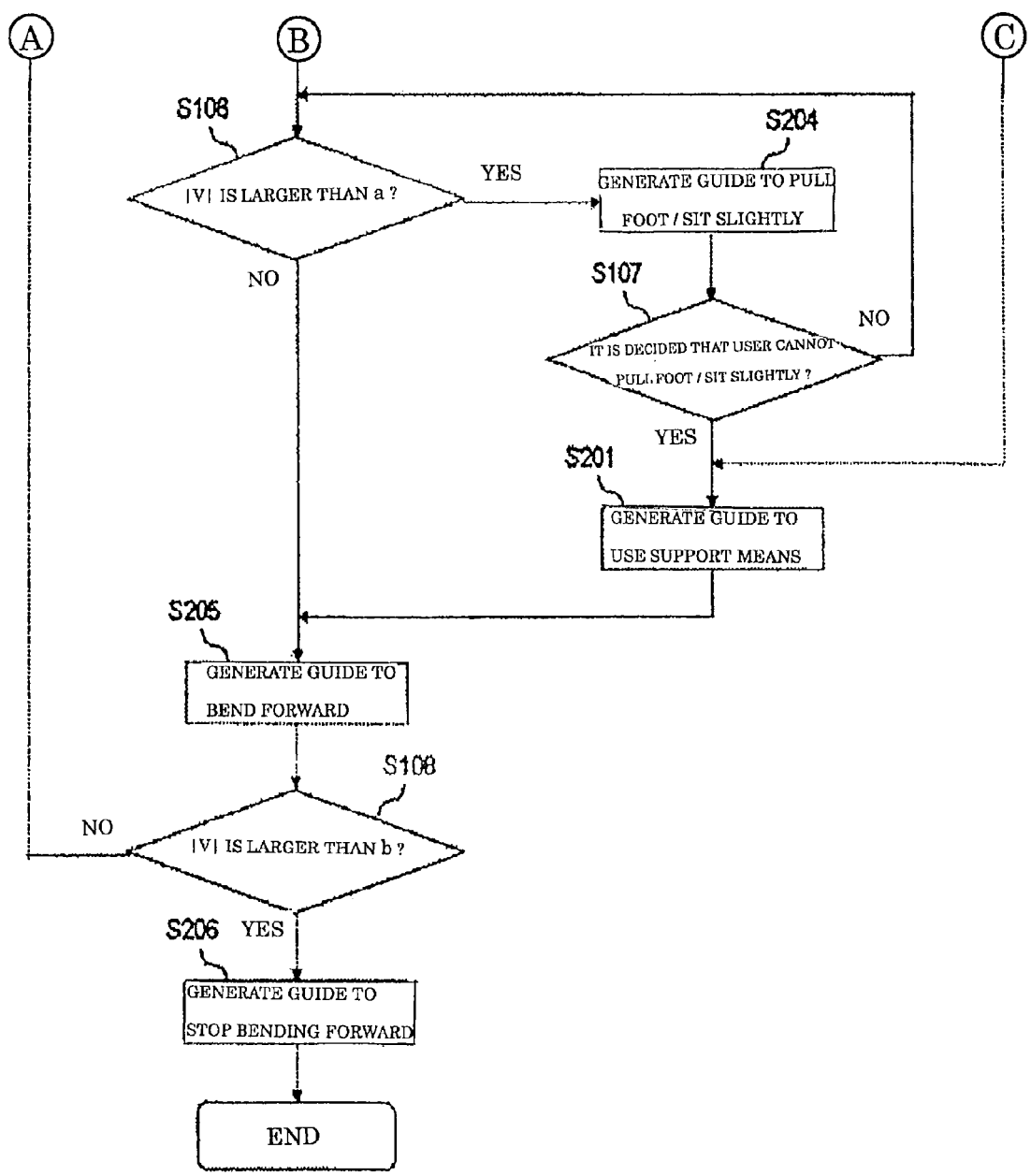

By referring to flow chart of FIGS. 11A and 11B, function of the guide information generation unit 225 of the second embodiment will be explained.

At S101, it is decided whether "user cannot bend knee" is set to any of right and left knees. If "user cannot bend knee" is set (Yes at S101), an outside of the base of support at the set side is specified as a position of support means, and a guide to use the support means is generated (S201). Here, if a fixed handrail exists at a range where the support means is positioned, a position of the fixed handrail is regarded as the position of support means. If the handrail does not exist at the range, a position to support by a stick (and so on) is regarded as the position of support means. Furthermore, if "user cannot bend knee" is not set to both right and left knees (No at S101), it is decided whether positions of toes of the user's right and left feet are aligned (S102).

If it is decided that the positions of toes are not aligned (Yes at S102), a recommendation position to align positions of toes of the user's right and left feet is set, and a guide to align the user's right and left feet is generated (S202). Here, the recommendation position is a position related to the user's front and back direction (x-axis) where x-coordinate of leg joint is smaller than x-coordinate of knee joint as several centimeters (at the user side) and x-coordinates of toes of right and left feet are aligned. Next, it is decided whether the user can align positions of toes of right and left feet (S103).

If it is decided that the user cannot align positions of toes of right and left feet (Yes at S103), a position of support means is set at one foot side positioned near the waist and the outside of the base of support, and a guide to use the support means is generated (S201). Furthermore, if it is decided that the user can align positions of toes of right and left feet (Yes at S103), processing is returned to S102. Here, at S103, a condition to decide that the user cannot align positions of toes of right and left feet (Yes at S103) is, for example, the case that positions of toes of right and left feet are not aligned after a predetermined time has passed from a generation time of the guide to align positions of toes, or the case that the user inputs a command to start guide by switch (and so on) while positions of toes of the user's right and left feet are not aligned.

Furthermore, at S102, if it is decided that the positions of toes are aligned (No at S102), it is decided whether the user's foot breadth (distance between the user's right and left feet) is suitable (S104). Here, at S102, even if positions of toes of right and left feet are shifted therebetween as several centimeters, it may be decided that the positions of toes are aligned.

If the foot breadth is not suitable (Yes at S104), a recommendation position of right and left feet is set, and a guide to change the foot breadth between right and left feet is generated (S203). The recommendation position is a position related to the user's right and left direction (y-axis) where a width between right leg joint and left leg joint is approximately equal to a shoulder width, and bilateral symmetry for the user's COG. Next, it is decided whether the user can change the foot breadth (S105).

If it is decided that the user cannot change the foot breadth (Yes at S105), a guide to use a support means is generated (S201). Furthermore, if it is decided that the user can change the foot breadth (No at 105), processing is returned to S104. Here, at S105, decision whether to change the foot breadth can be executed by a passing time or a switch input, in the same way as S103.

Furthermore, if the foot breadth is suitable (No at S104), a distance between the waist and the base of support is decided (S106). Moreover, at S104, for example, if the foot breadth is approximately equal to a width of the waist within a predetermined range, the foot breadth is decided to be suitable. If the foot breadth is narrower or wider than the width of the waist, the foot breadth is decided to be unsuitable.

If a magnitude |V| of the guide vector (a distance between the target position and the projection position of COG) is larger than a prescribed value "a" (Yes at S106), a guide to pull foot or sit slightly is generated (S204). Next, it is decided whether the user can pull foot/sit slightly (S107).

If it is decided that the user cannot pull foot/sit slightly (Yes at S107), a guide to use support means is generated (S201). Furthermore, if it is decided that the user can pull foot/sit slightly (No at S107), processing is returned to S106. Here, at S107, decision whether to pull foot/sit slightly can be executed by a passing time or a switch input, in the same way as S103 and S105.

Furthermore, If the magnitude |V| of the guide vector is larger than the prescribed value "a" (No at S106), a guide to bend forward (anterior inclination) the user's upper body (trunk) slowly is generated (S205). Here, the prescribed value "a" is set as a distance between the knee joint and the waist joint. Alternatively, the prescribed value "a" may be set based on the level set to the knee and the waist. For example, if the level set to the waist is "QUITE", the prescribed value "a" had better be smaller.

Above-mentioned steps are executed until the magnitude |V| of the guide vector is smaller than the prescribed value "b" (S108). If the magnitude |V| of the guide vector is smaller than the prescribed value "b" (Yes at S108), a guide to stop bending forward is generated (S206), and processing is completed.

The guide information generation unit 225 supplies each guide (generated as mentioned-above) to the guide output unit 230. For example, the guide output unit 230 presents content of the guide to the user by speech or information display. Here, if the support means does not exist at a suitable position (S201), a guide to call a helper may be generated. Furthermore, when the projection position of COG is over the target position before lifting-off buttocks, guide information may be generated toward a direction to return the projection position of COG. Furthermore, when buttocks lift-off are recognized during guiding, a guide to stop bending forward may be generated. The buttocks lift-off can be detected from positional relationship between the waist and a bearing surface of the seat part previously measured. Positions of the bearing surface and the handrail can be previously registered into the ROM 330 as environment information.

As a result, in advance of the stand-up motion, the user's posture can be suitable. Furthermore, by guiding positions of both feet to a suitable place, the user's stand-up motion from natural situation can be supported. Accordingly, the user's burden can be reduced through entire stand-up motion.

The Third Embodiment

Figure 12:
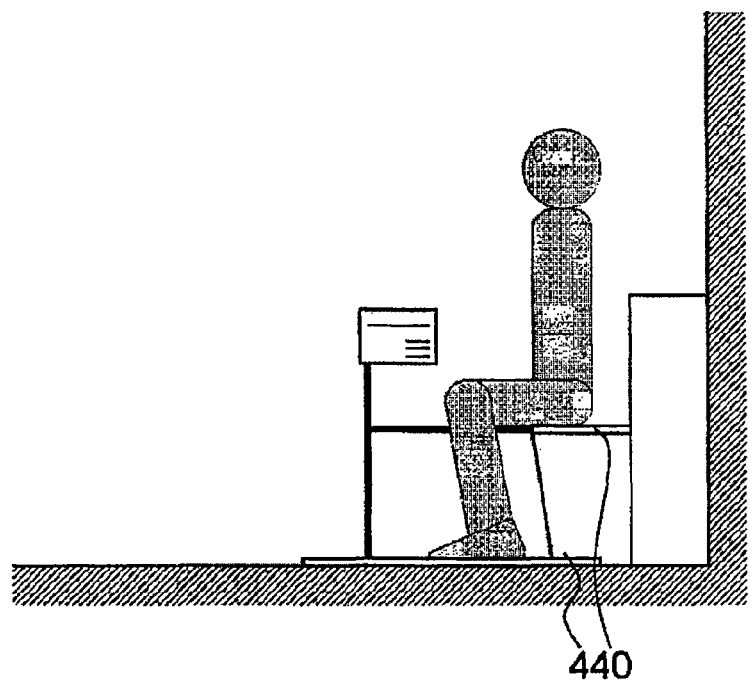
FIG. 12 is an overview diagram of the support apparatus according to the third embodiment.
Figure 13:
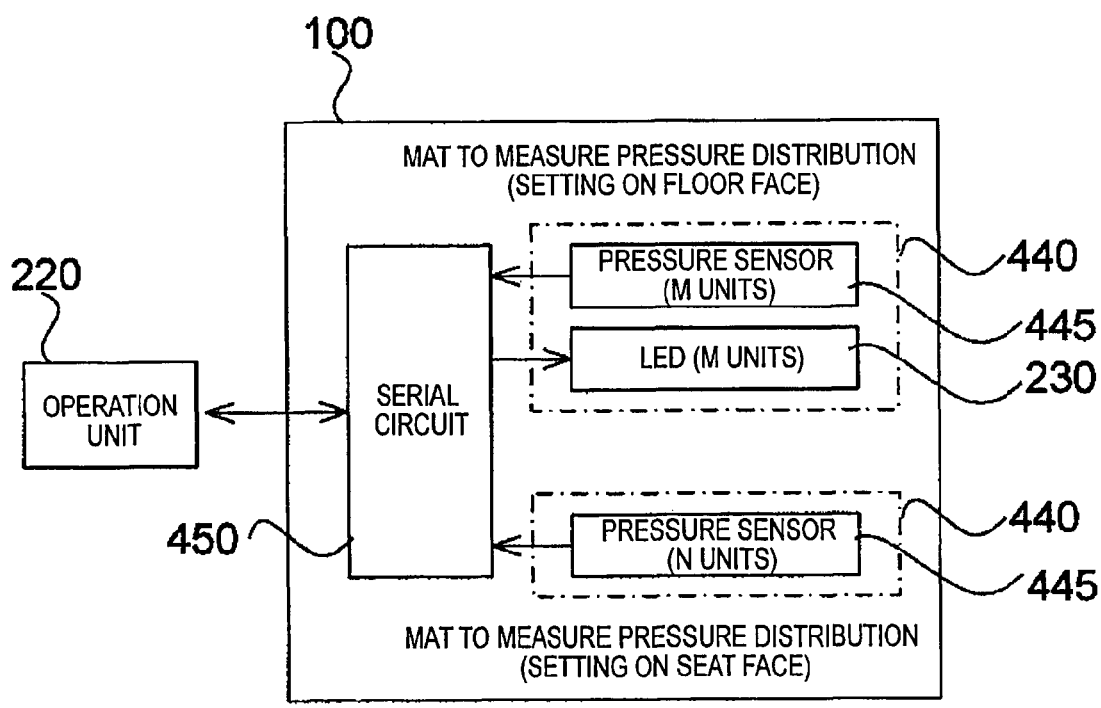
FIG. 13 is a block diagram of a measurement unit and a guide output unit according to the third embodiment.

By referring to FIGS. 12 and 13, the measurement unit 100 and the guide output unit 230 of the third embodiment will be explained.

The measurement unit 100 equips a mat 440 to measure pressure distribution and a serial circuit 450. The mat 440 having sheet-shape includes a plurality (M units) of pressure sensors 445 two-dimensionally disposed. The serial circuit 450 serially sends values of the plurality of pressure sensors 445 to the operation unit 220.

A plurality of mats 440 can be connected to the serial circuit 450. On a floor face adjacent to the seat part, the mat 440 is located. Furthermore, another mat 440 including pressure sensors 445 (N units) is located on the seat part. The serial circuit 450 hourly sends position information of the pressure sensor 445 (or ID information corresponding thereto) and measure pressure values to the operation unit 220.

From information of the mat 440 located on the floor face, the base of support-calculation unit 222 calculates contact positions of the user's right and left feet.

From position information of the pressure sensor 445 which has recognized the contact, the base of support-calculation unit 222 decides a contact region of both feet, and calculates a maximum and a minimum of each axis of the region as toe positions and heel positions respectively. Then, the base of support-calculation unit 222 calculates a base of support including a location region of both feet and a region surrounded by feature points.

Furthermore, the base of support-calculation unit 222 calculates coordinates of pressure center positions of right and left feet on the reference coordinate system as $(x_l, y_l)$ and $(x_r, y_r)$ respectively, and calculates a total (contact force) of pressures within the contact region of right and left feet as $f_l$ and $f_r$ respectively. Furthermore, from information of the mat 440 located on the seat, the base of support-calculation unit 222 calculates a coordinate $(x_b, y_b)$ of pressure center position of the buttocks, and calculates a total (contact force) $f_b$ of pressures within the contact region of the buttocks.

Here, assume that a position coordinate of each pressure sensor $m_i$ is $(x_{mi}, y_{mi})$, and a pressure (force per unit area) measured by the pressure sensor $m_i$ is $f_{mi}$. Each pressure center is calculated by following equation (1).

$$f_l = \sum_i^{\text{left foot region}} f_{mi}, \quad f_r = \sum_i^{\text{right foot region}} f_{mi}, \quad (1)$$

$$f_b = \sum_i^{\text{buttocks region}} f_{mi}$$

$$x_l = \frac{1}{f_l} \sum_i^{\text{left foot region}} x_{mi} \cdot f_{mi}, \quad y_l = \frac{1}{f_l} \sum_i^{\text{left foot region}} y_{mi} \cdot f_{mi}$$

$$x_r = \frac{1}{f_r} \sum_i^{\text{rightt foot region}} x_{mi} \cdot f_{mi}, \quad y_{rl} = \frac{1}{f_r} \sum_i^{\text{rightt foot region}} y_{mi} \cdot f_{mi}$$

$$x_b = \frac{1}{f_b} \sum_i^{\text{buttocks region}} x_{mi} \cdot f_{mi}, \quad y_{bl} = \frac{1}{f_b} \sum_i^{\text{buttocks region}} y_{mi} \cdot f_{mi}$$

Following equation (2) represents a balance relationship among a moment of contact force at pressure center position of right and left feet, a moment of contact force at pressure center position of buttocks, and a moment of self-weight at the user's COG. From the balance relationship, the center of gravity-calculation unit 221 calculates a position to balance these moments as a projection position of COG. Here, each moment is a moment around the origin on the reference coordinate system.

$$x_p = (f_l x_l + f_r x_r + f_b x_b)/(f_l + f_r + f_b)$$

$$y_p = (f_l y_l + f_r y_r + f_b y_b)/(f_l + f_r + f_b) \quad (2)$$

The guide output unit 230 comprises indicator parts (LED) of M units two-dimensionally disposed on the mat 440 located on the floor face. This indicator part specifies a direction for the user to bend the upper body or an amount for the user to bend the waist forward. As a result, the direction to bend the upper body or the amount to bend the waist forward can be visually presented to the user. Furthermore, a reference point to correct feet-location position can be presented to the user via light emission. Accordingly, effective guide can be realized.

The Fourth Embodiment

Figure 14:
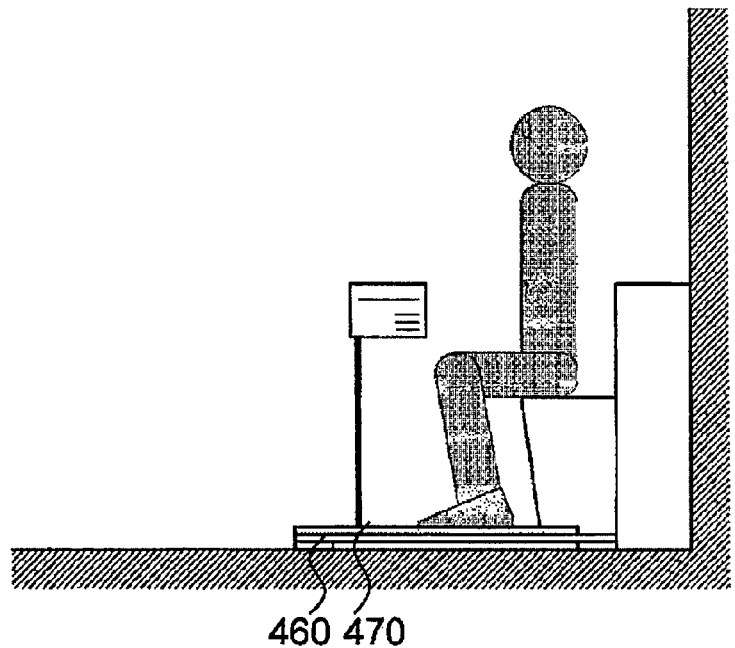
FIG. 14 is an overview diagram of the support apparatus according to the fourth embodiment.
Figure 15:
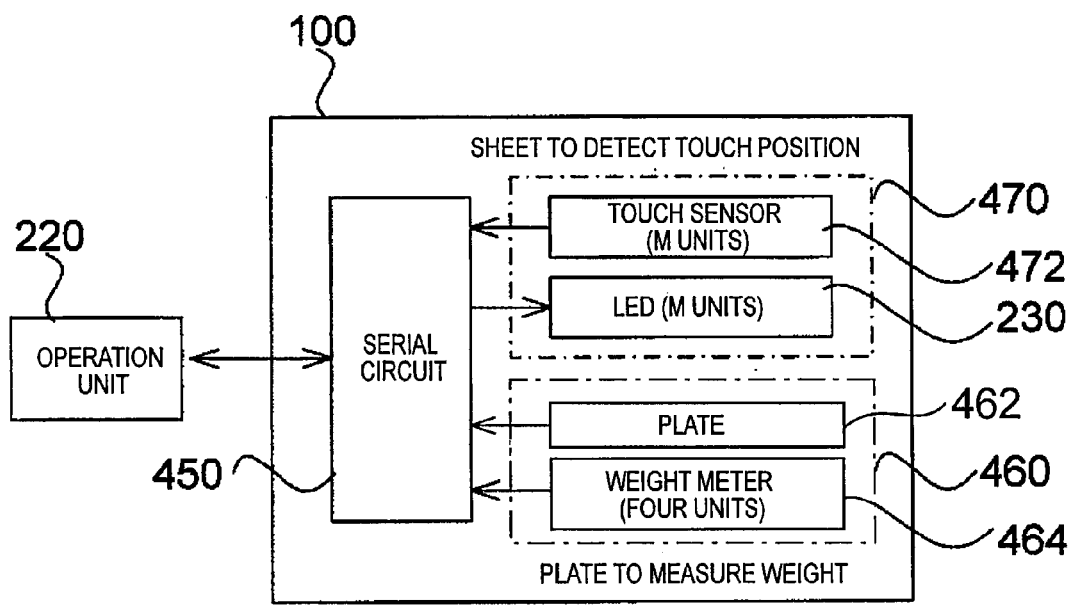
FIG. 15 is a block diagram of the measurement unit and the guide output unit according to the fourth embodiment.

By referring to FIGS. 14 and 15, the measurement unit 100 and the guide output unit 230 of the fourth embodiment will be explained.

The measurement unit 100 equips a plate 460 to measure weight and a sheet 470 to detect touch position. The plate 460 includes a plate 462 and a plurality of (For example, four units) weight meters 464 to measure a force supported by the plate 462. On the sheet 470, touch sensors 472 (M units) to detect a touch position are two-dimensionally disposed.

The sheet 470 is located on the plate 460 adjacent to the seat part. The plate 460 is located on the floor face so as to place the seat part thereon.

From a positional relationship among four weight meters 464 and a weight measured by respective weight meters, the center of gravity-calculation unit 221 calculates a projection position of COG of a person or an object placed on the plate 460. Namely, on condition that the seat part is placed on the plate 460, by offset-adjusting so that the weight measured by the plate 460 is equal to zero, a projection position of COG of the user placed on the plate 460 can be calculated.

For example, assume that weights measured by four weight meters are $M_1$, $M_2$, $M_3$, $M_4$ respectively, and position coordinates of four weight meters are $(x_1,y_1)$ $(x_2,y_2)$ $(x_3,y_3)$, $(x_4,y_4)$ respectively. The projection position of COG is calculated by following equation (3).

$$x_p=(M_1 \cdot x_1+M_2 \cdot x_2+M_3 \cdot x_3+M_4 \cdot x_4)/(M_1+M_2+M_3+M_4)$$

$$y_p=(M_1 \cdot y_1+M_2 \cdot y_2+M_3 \cdot y_3+M_4 \cdot y_4)/(M_1+M_2+M_3+M_4) \quad (3)$$

The base of support-calculation unit 222 calculates a base of support from information of the touch position. Namely, from position information of touch sensors 472 which has recognized the touch, a touch region is decided, and a maximum and a minimum of each axis of the touch region are calculated as toe positions and heel positions respectively. Based on these data, the base of support is calculated.

By above-mentioned method, without two mats 440 which are relatively expensive, a position and a projection position of COG of the base of support can be calculated using the plate 460 and the sheet 470 which are relatively cheep. Naturally, the base of support may be calculated using the camera 110 instead of the sheet 470. Furthermore, it is needless to say that the measurement unit 100 is adaptively combined therewith.

The guide output unit 230 comprises indicator parts (LED) of M units two-dimensionally disposed on the sheet 470 located on the floor face. This indicator part specifies a direction for the user to bend the upper body or an amount for the user to bend the waist forward. As a result, the direction to bend the upper body or the amount to bend the waist forward can be visually presented to the user. Furthermore, a reference point to correct feet-location position can be presented to the user via light emission. Accordingly, effective guide can be realized.

Moreover, from position information of the touch sensor 472 which has recognized the touch, the base of support-calculation unit 222 may decide a touch region and calculate a base of support including the entire touch region. As a result, by extending a range in which the target position is settable, the stand-up motion can be flexibly supported.

The Fifth Embodiment

Figure 16:
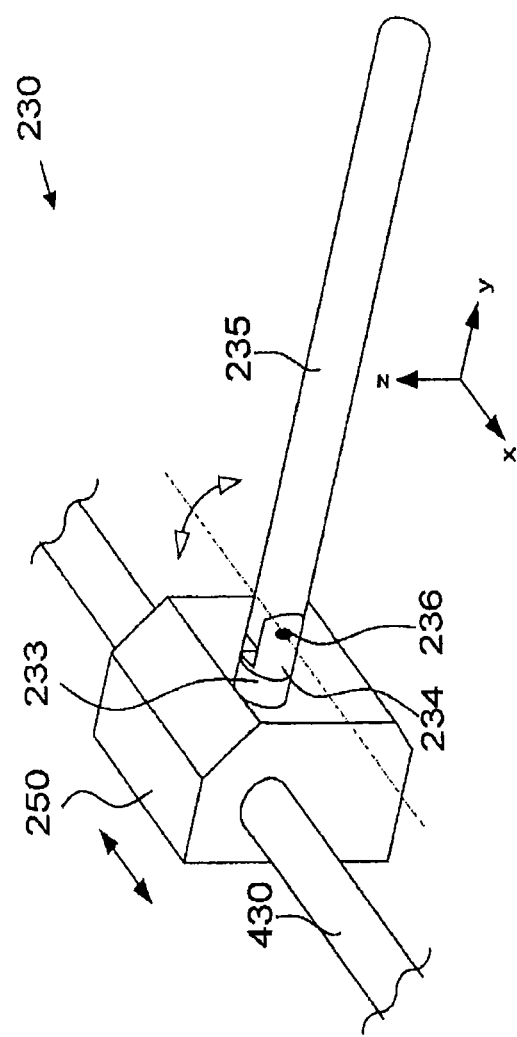
FIG. 16 is a perspective diagram of the guide output unit according to the fifth embodiment.
Figure 17:
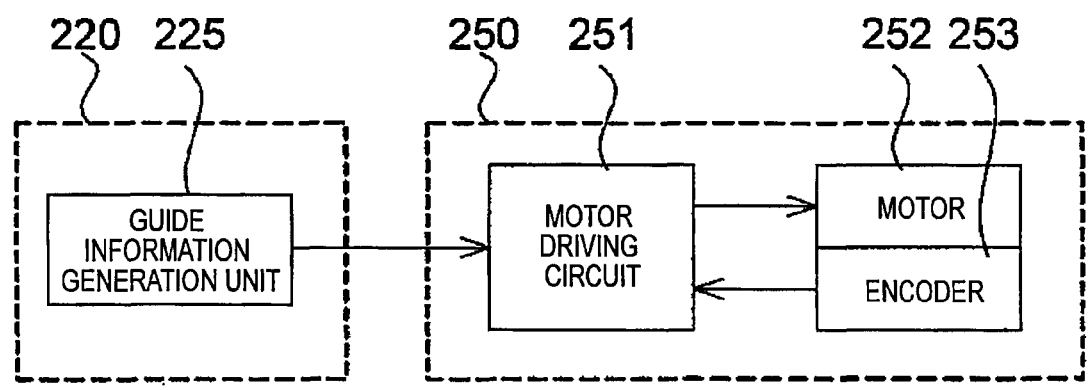
FIG. 17 is a block diagram of a moving unit according to the fifth embodiment.

By referring to FIGS. 16 and 17, the guide output unit 230 of the fifth embodiment will be explained. In the fifth embodiment, as a timing to support the stand-up motion, in addition to a time until the user's buttocks are lifted off from the seat part, a time until the user stars moving after standing up is targeted.

The guide output unit 230 equips a moving unit 250, FT sensor 233, a support unit 234, and a grasp unit 235. The moving unit 250 having box-shape is movable along a handrail fixed on the wall. In the moving unit 250, a motor driving circuit 251, a motor 352, and an encoder 253, are equipped. A rubber roller is rotationally connected to a shaft of the motor 252 via a gear. By the rubber roller rotating in contact with the handrail 430, the moving unit 250 can be moved along a longitudinal direction (x-axis direction) of the handrail 430.

The encoder 253 is equipped with the shaft of the motor 252, and a rotation angle of the motor 252 can be detected thereby. The motor driving circuit 251, the motor 252, and the encoder 253, form a closed loop circuit. By controlling the rotation angle of the motor 252 by the motor driving circuit 251, a moving amount of the moving unit 250 can be controlled. Here, based on a guide moving amount generated by the guide information generation unit 225 in the operation unit 220, a command voltage value to drive the motor 252 is calculated and sent to the motor driving circuit 251.

FT sensor 233 having cylinder-shape is equipped with the moving unit 250. At an opposite face of the FT sensor 233 fixed with the moving unit 250, the support unit 234 is fixed. A rotation shaft 236 is set at the support unit 234. The grasp unit 235 having stick-shape is rotationally equipped around and via the rotation shaft 236. The grasp unit 235 can be rotated around the rotation shaft 236. Namely, when the grasp unit 235 is used for guide, it can be extended so that the longitudinal direction is y-axis direction. Furthermore, when the grasp unit 235 is not used or when the user sits down the seat part, it can be contained so that the longitudinal direction is z-axis direction.

The FT sensor 233 can detect a force added to x-axis, y-axis and z-axis directions, and a torque added to around respective axes. By this FT sensor 233, magnitude and direction of force added to the grasp unit 235, and a point of action thereof, can be detected. In the center of gravity-calculation unit 221 of the operation unit 220, from information sent by the measurement unit 100 and the FT sensor 233, the user's center of gravity can be more accurately calculated.

Next, a guide method by the guide output unit 230 of the fifth embodiment will be explained. While the user is posturing sit-down, the moving unit 250 is controlled on the fixed handrail so that the grasp unit 235 (of the guide output unit 230) is adjacently positioned over the user's knee joint.

After outputting a command to start posture-guide, the moving unit 250 is controlled with velocity in proportion to a magnitude of the guide vector. In this case, immediately after starting guide, the moving unit 250 is controlled so as to be slowly equal to a predetermined velocity. Furthermore, after starting guide, the user's hands are guided earlier than the user's upper body. Accordingly, the velocity therewith may be higher to some extent.

When the user's COG is nearer a predetermined position, a magnitude of the guide vector becomes smaller, and the velocity to move the moving unit 250 becomes lower based on the magnitude. Accordingly, the guide of which uncomfortable feeling is little can be realized without sudden stop. Furthermore, if the user's COG cannot be guided bilaterally (For example, when the user cannot bend any of right and left knees), the guide handrail had better be controlled to a position set as the recommendation position of the support means.

After the measurement unit 100 detects the user's buttocks lift-off, the moving unit 250 is controlled to be at the predetermined velocity. As a result, the user's moving after stand-up motion can be supported.

By guide means with the handrail 430, the guide can be realized without the user being unconscious of the projection position of COG. Accordingly, the user's difficulty can be reduced. Furthermore, by grasping the grasp unit 235 with the user's hand, the base of support is enlarged. Accordingly, stability of stand-up motion is improved.

Moreover, in the fifth embodiment, the moving unit 250 may be incorporated into the main unit 200. Furthermore, the camera 110 or the near infrared-ray sensor 120 may be incorporated into the lower side of the moving unit 250 or the handrail 430.

According to the support apparatus or the support method of at least one embodiment mentioned-above, balance of load occurred at body part with stand-up motion can be adjusted. As a result, while practical use of remaining physical ability is urged to the user, the user's stand-up motion can be supported.

In above-mentioned embodiments, support of stand-up motion in toilet space was assumed and explained. However, the support is not limited to this example. For example, stand-up motion from sit-down situation (such as stand-up motion in bath, stand-up motion from bed) may be supported. Furthermore, the support apparatus of the present embodiment has a function to distribute physical loads of knee and waist. Accordingly, by intentionally setting to apply load to a specific physical part, the support apparatus can be used to aim at training of the specific physical part.

While certain embodiments have been described, these embodiments have been presented by way of examples only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A support apparatus comprising:
    an input unit to designate a distribution of a load between a right body part and a left body part of a user, the load being occurred at body parts of the user by a stand-up motion of the user;
    a measurement unit to measure each position of body parts of the user;
    a processor that, by using a control program stored in a memory,
    calculates a projection position of a center of gravity of the user onto a floor, based on the position,
    calculates a target position based on the distribution, the target position being nearer to one of the right body part and the left body part of the user than the other of the right body part and the left body part of the user, a larger value of the distribution being designated to the one of the right body part and left body part, a smaller value of the distribution being designated to the other of the right body part and left body part, and
    calculates a direction from the projection position to the target position; and
    an output unit to output a designation direction for the user to bend an upper body of the user in advance of the stand-up motion, based on the direction.

2. The support apparatus according to claim 1, wherein
    the input unit further designates a distribution of the load between a front body part and a back body part of the user, and
    the processor further calculates the target position based on the distribution,
    the target position being nearer to one of the right body part and the left body part of the user than the other of the right body part and the left body part of the user, a larger value of the distribution being designated to the one of the right body part and left body part, a smaller value of the distribution being designated to the other of the right body part and left body part,
    the target position being farther from one of the front body part and the back body part of the user than the other of the front body part and the back body part of the user, a larger value of the distribution being designated to the one of the right body part and left body part, a smaller value of the distribution being designated to the other of the right body part and left body part.

3. The support apparatus according to claim 2, wherein
    the distribution of the load between the right body part and the left body part of the user represents a distribution of the load occurred at a right knee and a left knee of the user, and
    the distribution of the load between the front body part and the back body part of the user represents a distribution of the load occurred at a knee and a waist of the user.

4. A support apparatus comprising:
    an input unit to designate a distribution of a load between a front body part and a back body part of a user, the load being occurred at body parts of the user by a stand-up motion of the user;
    a measurement unit to measure each position of body parts of the user;
    a processor that, by using a control program stored in a memory,
    calculates a projection position of a center of gravity of the user onto a floor, based on the position,
    calculates a target position based on the distribution, the target position being farther from one of the front body part and the back body part of the user than the other of the front body part and the back body part of the user, a larger value of the distribution being designated to the one of the right body part and left body part, a smaller value of the distribution being designated to the other of the right body part and left body part, and
    calculates a direction from the projection position to the target position; and
    an output unit to output a designation direction for the user to bend an upper body of the user in advance of the stand-up motion, based on the direction.

5. The support apparatus according to claim 1, wherein
    the processor further calculates a region surrounded by both feet of the user that contact on the floor.

6. The support apparatus according to claim 1, wherein the processor further
calculates a distance between the projection position and the target position, and
generates a first designation to urge the user to correct a posture of the user so that the distance is smaller than a reference distance,
wherein the output unit outputs the first designation.

7. The support apparatus according to claim 6, wherein the processor further generates a second designation to urge the user to correct a position of both feet of the user so that the region is nearer to a reference region, and
the output unit outputs the second designation.

8. The support apparatus according to claim 1,
wherein the processor further calculates the center of gravity by calculating a total of moment vectors multiplied a weight ratio of each body part with the position, and calculates a projection position of the center of gravity onto the floor.

9. The support apparatus according to claim 8, wherein
the measurement unit includes a camera to obtain an image of the user,
the output unit is a projector to project the designation direction onto the floor, and
the camera and the projector are equipped as one unit.

10. The support apparatus according to claim 1, wherein
the measurement unit to measures a first distribution of contact pressure of both feet of the user and a second distribution of contact pressure of buttocks of the user, and
the processor further calculates the projection position as a position to balance a moment by a first contact force at a first pressure center of the first distribution, a moment by a second contact force at a second pressure center of the second distribution, and a moment by a self-weight of the user.

11. The support apparatus according to claim 1, wherein
the measurement unit includes a plurality of weight meters and a plurality of touch sensors disposed on the floor, and
the processor further
calculates the projection position as a position to balance a moment by weights measured by the weight meters, and a moment by a self-weight of the user, and
calculates coordinates of the region by using information from the touch sensors.

12. The support apparatus according to claim 10, wherein
the measurement unit is located on a sheet, and
the output unit comprises a plurality of indicators disposed on the sheet, and makes an indicator that specifies the designation direction emit light.

13. The support apparatus according to claim 11, wherein
the measurement unit is located on a sheet, and
the output unit comprises a plurality of indicators disposed on the sheet, and makes an indicator that specifies the designation direction emit light.

14. The support apparatus according to claim 1, wherein
the output unit comprises a handrail including a plurality of indicators, and makes an indicator that specifies the designation direction emit light.

15. The support apparatus according to claim 1, wherein
the processor further calculates a distance between the projection position and the target position, and
the output unit is installed onto a handrail, and comprises a grasp unit movably disposed along a longitudinal direction of the handrail, and
a moving unit to make the grasp unit move based on the distance.

16. A support method comprising:
designating by an input unit, a distribution of a load between a right body part and a left body part of a user, the load being occurred at body parts of the user by a stand-up motion of the user;
measuring by a measurement unit, each position of body parts of the user;
calculating by a processor using a control program stored in a memory, a projection position of a center of gravity of the user onto a floor, based on the position;
calculating by the processor, a target position in the region based on the distribution, the target position being nearer to one of the right body part and the left body part of the user than the other of the right body part and the left body part of the user, a larger value of the distribution being designated to the one of the right body part and left body part, a smaller value of the distribution being designated to the other of the right body part and left body part;
calculating by the processor, a direction from the projection position to the target position; and
outputting by an output unit, a designation direction for the user to bend an upper body of the user in advance of the stand-up motion, based on the direction.

17. A support method comprising:
designating by an input unit, a distribution of a load between a front body part and a back body part of a user, the load being occurred at body parts of the user by a stand-up motion of the user;
measuring by a measurement unit, each position of body parts of the user;
calculating by a processor using a control program stored in a memory, a projection position of a center of gravity of the user onto a floor, based on the position;
calculating by the processor, a target position in the region based on the distribution, the target position being farther from one of the front body part and the back body part of the user than the other of the front body part and the back body part of the user, a larger value of the distribution being designated to the one of the right body part and left body part, a smaller value of the distribution being designated to the other of the right body part and left body part;
calculating by the processor, a direction from the projection position to the target position; and
outputting by an output unit, a designation direction for the user to bend an upper body of the user in advance of the stand-up motion, based on the direction.

* * * * *